United States Patent
Bae et al.

(10) Patent No.: US 10,251,674 B2
(45) Date of Patent: Apr. 9, 2019

(54) MANUAL FOLLICLE-TRANSPLANTING HAIR TRANSPLANTER FOR INCREASING GRAFT SURVIVAL RATE

(71) Applicants: Electronics and Telecommunications Research Institute, Daejeon (KR); Kyungpook National University Industry-Academic Cooperation Foundation, Daegu (KR)

(72) Inventors: Tae Wuk Bae, Daegu (KR); Yong Chul Jung, Daegu (KR); Kyu Hyung Kim, Daegu (KR); Moon Kyu Kim, Daegu (KR); Jung Chul Kim, Daegu (KR); Jung Wook Suh, Daegu (KR); Hyung Soo Lee, Daegu (KR); Eun Chang Choi, Daegu (KR); Dae Sik Kim, Daejeon (KR); Chang Hyuk Hong, Daegu (KR)

(73) Assignees: Electronics and Telecommunications Research Institute, Daejeon (KR); Kyungpook National University Industry-Academic Cooperation Foundation, Daegu (KR)

(*) Notice: Subject to any disclaimer, the term of this patent is extended or adjusted under 35 U.S.C. 154(b) by 156 days.

(21) Appl. No.: 15/137,600

(22) Filed: Apr. 25, 2016

(65) Prior Publication Data

US 2017/0020564 A1   Jan. 26, 2017

(30) Foreign Application Priority Data

Jul. 22, 2015   (KR) ........................ 10-2015-0103801

(51) Int. Cl.
*A61B 17/34*   (2006.01)
*A61B 17/3205*   (2006.01)
*A61B 17/00*   (2006.01)

(52) U.S. Cl.
CPC .... *A61B 17/3468* (2013.01); *A61B 17/32053* (2013.01); *A61B 2017/00752* (2013.01)

(58) Field of Classification Search
CPC .......... A61B 17/3468; A61B 17/32053; A61B 2017/00752
See application file for complete search history.

(56) References Cited

U.S. PATENT DOCUMENTS 6,461,369 B1   10/2002   Kim
7,144,406 B2   12/2006   Pak et al.
(Continued)

FOREIGN PATENT DOCUMENTS

KR   10-0417829 B1   2/2004

*Primary Examiner* — Phong Son H Dang
(74) *Attorney, Agent, or Firm* — William Park & Associates Ltd.

(57) ABSTRACT

Provided is a manual follicle-transplanting hair transplanter for increasing a graft survival rate. The manual follicle-transplanting hair transplanter includes a needle member having a lower end containing a follicle to be transplanted and having a head having a larger diameter than a portion below the head at an upper end thereof, a rod member inserted into the needle member and having a push portion having a larger diameter than a portion below the push portion at an upper end thereof, an inner body configured to contain the needle member and limit downward movement of the needle member, and an outer body configured to contain the inner body and limit upward movement of the needle member. The needle member is automatically withdrawn when a compressed spring disposed in the inner body expands and pushes up a lower surface of the head.

8 Claims, 8 Drawing Sheets

(56) References Cited

U.S. PATENT DOCUMENTS

2014/0188150 A1\* 7/2014 Oc ............................ A61F 2/10
606/187
2016/0213400 A1\* 7/2016 Oc ..................... A61B 17/3468

\* cited by examiner

MANUAL FOLLICLE-TRANSPLANTING HAIR TRANSPLANTER FOR INCREASING GRAFT SURVIVAL RATE

CROSS-REFERENCE TO RELATED APPLICATION

This application claims priority to and the benefit of Korean Patent Application No. 10-2015-0103801, filed on Jul. 22, 2015, the disclosure of which is incorporated herein by reference in its entirety.

BACKGROUND

1. Field of the Invention

The present invention relates to a follicle-transplanting hair transplanter, and more particularly, to a manual follicle-transplanting hair transplanter for increasing a graft survival rate which enables maximization of a survival rate of transplanted follicles and also minimization of transplantation surgeon fatigue in a follicle transplantation process.

2. Discussion of Related Art

A large number of people suffer from alopecia, that is, excessive loss of hair, such as the hair on one's head.

Here, a region of hair loss is conspicuous compared to a region of no hair loss. Therefore, some alopecia patients wear wigs for beauty, thereby preventing regions of hair loss from being conspicuous.

However, it is inconvenient to wear and manage a wig, and a wig does not blend with existing hair and thus leads to a sense of heterogeneity. Also, a region on which a wig can be put is limited.

For these reasons, alopecia patients who have hair transplantation in regions of hair loss are increasing lately.

Since hair transplantation results in long-term maintenance of the effect of covering a region of hair loss and no sense of heterogeneity from existing hair, the number of alopecia patients who consider hair transplantation is constantly increasing.

Meanwhile, a manual follicle-transplanting hair transplanter is generally used in a hair transplantation procedure.

Here, an existing manual follicle-transplanting hair transplanter includes a needle member containing a follicle and a rod member for pressurizing the follicle contained in the needle member. In the process of inserting the needle member containing the follicle into skin and then withdrawing the needle member, the follicle is transplanted into the skin by pressurizing the follicle inserted into the skin with the rod member.

Using such an existing manual follicle-transplanting hair transplanter, it is possible to transplant a follicle in a region of hair loss. However, during a withdrawal process of the needle member, the needle member, etc. is unnecessarily moved by a transplantation surgeon's hand movements, etc., and the follicle is frequently withdrawn, that is, frequently comes out, together with the needle member. Therefore, depths of embedded follicles are different, and follicles which have not been deeply embedded in skin have difficulty in surviving. Consequently, a graft survival rate after follicle transplantation is low.

Also, in the case of the existing manual follicle-transplanting hair transplanter, a body containing the needle member is lifted by a transplantation surgeon's hand movements, that is, with the transplantation surgeon's thumb, index finger, etc., to withdraw the needle member. Therefore, when transplanting hundreds to thousands of follicles into a region of hair loss, the transplantation surgeon feels considerable fatigue due to repeated hand movements, and transplantation surgeons who work for a long period may suffer from a musculoskeletal disease.

For the aforementioned reasons, development of a manual follicle-transplanting hair transplanter which enables maximization of the survival rate of transplanted follicles by uniformizing depths of follicles embedded in skin and also minimization of transplantation surgeon fatigue in a follicle transplantation process is under way in the corresponding field, but satisfactory results have not been obtained so far.

SUMMARY OF THE INVENTION

The present invention is directed to providing a manual follicle-transplanting hair transplanter which enables maximization of the survival rate of transplanted follicles and also minimization of transplantation surgeon fatigue in a follicle transplantation process.

According to an aspect of the present invention, there is provided a manual follicle-transplanting hair transplanter including: a needle member having a lower end containing a follicle to be transplanted and having a head having a larger diameter than a portion below the head at an upper end thereof; a rod member inserted into the needle member and having a push portion having a larger diameter than a portion below the push portion at an upper end thereof; an inner body configured to contain the needle member and limit downward movement of the needle member; and an outer body configured to contain the inner body and limit upward movement of the needle member. The needle member is automatically withdrawn when a compressed spring disposed in the inner body expands and pushes up a lower surface of the head.

The head may have bumps on two opposite side surfaces.

The inner body may have openings into which the bumps of the head are inserted in two opposite side surfaces.

The inner body may have a seating surface for supporting a lower end of the spring in a lower portion thereof.

The inner body may have a support member supporting an upper end of the compressed spring.

The support of the support member may be released by pressurization from the outer body.

A part of the support member may be exposed to an outside of the outer body and directly pressurized.

The support member may be indirectly pressurized when a push member provided in the outer body is pressurized.

The support member may be disposed on one side or two opposite sides of the inner body.

The support member may have a protrusion which is catchable at the upper end of the compressed spring.

The support member may be coupled to the inner body to be movable into or out of the inner body.

The outer body may have a protruding jaw at an inner circumferential surface thereof.

The outer body may have a separable closure cap at a lower end thereof.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

Figure 1:
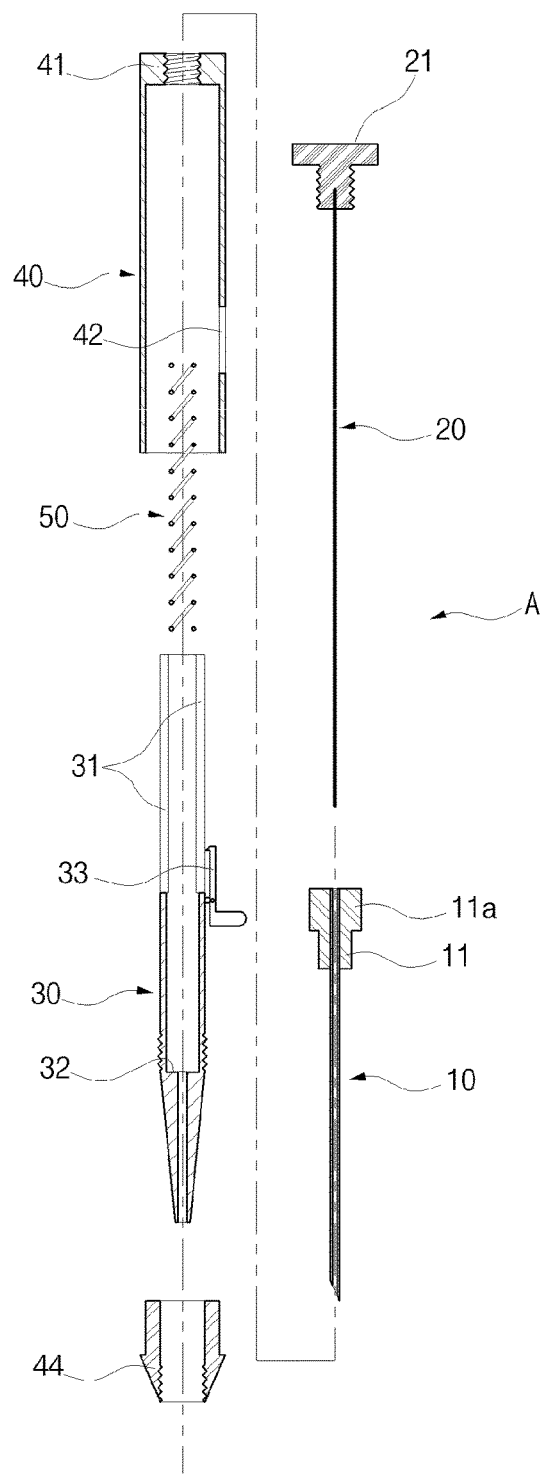
FIG. 1 is an exploded cross-section view illustrating a structure of a manual follicle-transplanting hair transplanter for increasing a graft survival rate according to an exemplary embodiment of the present invention.
Figure 2:
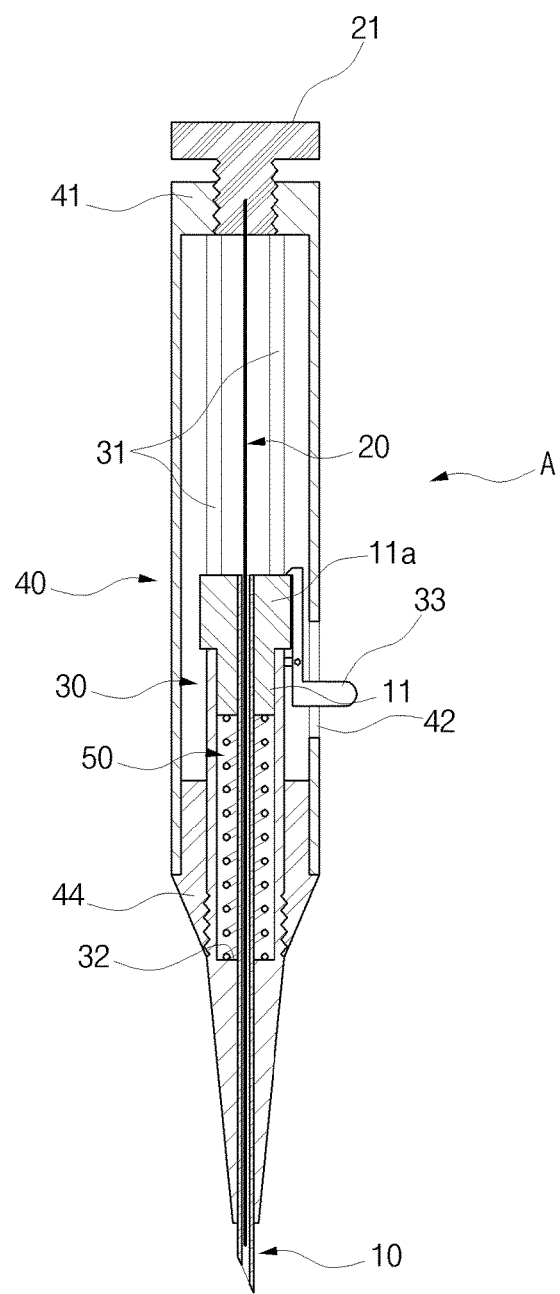
FIG. 2 is a cross-section view illustrating a structure of the follicle-transplanting hair transplanter in a combined state according to an exemplary embodiment of the present invention.

As shown in FIGS. 1 and 2, a manual follicle-transplanting hair transplanter A for increasing a graft survival rate according to an exemplary embodiment of the present invention includes a needle member 10, a rod member 20, an inner body 30, an outer body 40, and a spring 50.

The needle member 10 contains a follicle 100 to be transplanted in a lower end thereof.

Since the follicle 100 to be transplanted is contained in the lower end of the needle member 10, when the lower end of the needle member 10 is inserted into skin, the follicle 100 in the needle member 10 is inserted into the skin.

This needle member 10 has a head 11 having a larger diameter than a portion below the head 11 at an upper end thereof.

Since the needle member 10 has the head 11 having a larger diameter than the portion below the head 11 at the upper end thereof, the compressed spring 50 expands, and an upper end thereof pushes up the head 11, so that the needle member 10 may withdraw. Here, the head 11 has bumps 11a on two opposite sides.

Since the head 11 has the bumps 11a on the two opposite side surfaces, the bumps 11a are caught at lower ends of openings 31 provided in the inner body 30, and thus downward movement of the needle member 10 is limited in the inner body 30.

The rod member 20 is inserted into the needle member 10.

Since the rod member 20 is inserted into the needle member 10, when a lower end of the rod member 20 protrudes from the lower end of the needle member 10, the follicle 100 contained in the lower end of the needle member 10 is pressurized. In other words, the follicle 100 inserted into the skin is pressurized by the rod member 20, and thus is stably embedded in the skin.

This rod member 20 has a push portion 21 having a larger diameter than a portion below the push portion 21 at an upper end thereof.

Since the rod member 20 has the push portion 21 having a larger diameter than the portion below the push portion 21 at the upper end thereof, when the push portion 21 is pushed with any one of fingers of a transplantation surgeon, the needle member 10 is easily inserted into the skin.

The inner body 30 contains the needle member 10 and limits downward movement of the needle member 10.

This inner body 30 has the openings 31 on two opposite side surfaces.

Since the inner body 30 has the openings 31 on the two opposite side surfaces, when the bumps 11a are caught at the lower ends of the openings 31, downward movement of the needle member 10 is limited. Also, since the bumps 11a provided at the head 11 of the needle member 10 are inserted through the openings 31, the needle member 10 may be contained in the inner body 30 although the bumps 11a are provided at the head 11.

The inner body 30 has a seating surface 32 which supports a lower end of the spring 50 in a lower portion thereof.

Since the inner body 30 has the seating surface 32 which supports the lower end of the spring 50 in the lower portion thereof, the spring 50 may be compressed or may expand in the inner body 30.

The inner body 30 has a support member 33 which supports an upper end of the compressed spring 50.

Since the inner body 30 has the support member 33 supporting the upper end of the compressed spring 50, the spring 50 may be kept compressed. Here, the support for the spring 50 through the support member 33 is released by pressurization from the outer body 40.

When the support for the spring 50 through the support member 33 is released by pressurization from the outer body 40, the compressed spring 50 may expand. Here, a part of the support member 33 may be exposed to the outside of the outer body 40 and directly pressurized. In other words, an opening 42 may be formed in the outer body 40, and a part of the support member 33 may be exposed through the opening 42, so that the support member 33 may be directly pressurized.

Also, the support member 33 may be indirectly pressurized when a push member 43 provided at the outer body 40 is pressurized. In other words, a part of the push member 43 provided on an outer surface of the outer body 40 is moved in the outer body 40 through the opening 42 formed in the outer body 40 and comes in contact with the support member 33, so that the support member 33 may be indirectly pressurized.

Figure 7:
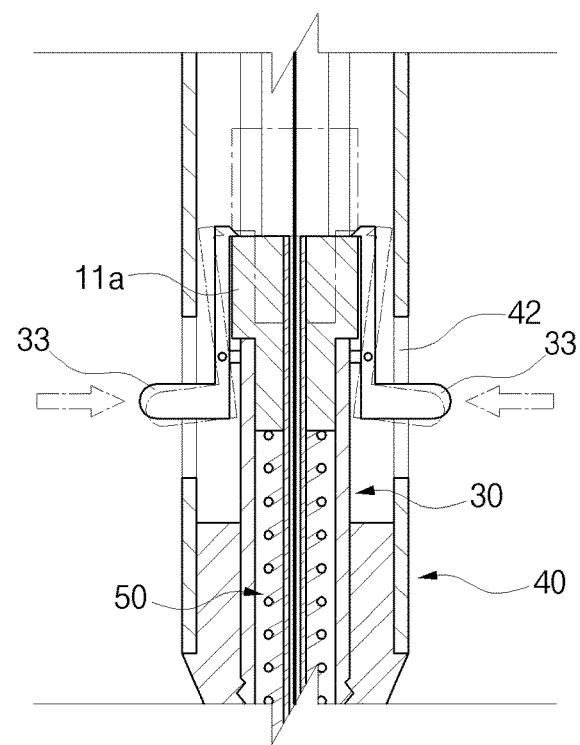
FIG. 7 is an example diagram showing another form of a support member according to an exemplary embodiment of the present invention.

Support members 33 may be disposed on two opposite sides of the inner body 30 as shown in FIG. 7.

When the support members 33 are disposed on the two opposite sides, it is possible to support two opposite sides of the compressed spring 50 with the support members 33, and thus support for the spring 50 through the support member 33 is stabilized.

Meanwhile, the support member 33 has a protrusion 33a which may be caught at the upper end of the compressed spring 50.

Since the support member 33 has the protrusion 33a which may be caught at the upper end of the compressed spring 50, when the protrusion 33a is caught at the upper end of the compressed spring 50, the upper end of the compressed spring 50 may be supported by the support member 33.

The support member 33 is coupled to the inner body 30 to be movable into or out of the inner body 30.

Since the support member 33 is coupled to the inner body 30 to be movable into or out of the inner body 30, when the support member 33 is moved outward by direct or indirect pressurization and the protrusion 33*a* deviates from the upper end of the spring 50, the support for the spring 50 through the support member 33 may be released.

The outer body 40 contains the inner body 30 and limits upward movement of the needle member 10.

This outer body 40 has a protruding jaw 41 at an upper end of an inner circumferential surface thereof.

Since the outer body 40 has the protruding jaw 41 on the upper end of the inner circumferential surface thereof, when the bumps 11*a* are caught at the protruding jaw 41, upward movement of the needle member 10 is limited.

The outer body 40 has a closure cap 44 at a lower end thereof.

Since the outer body 40 has the closure cap 44 at the lower end thereof, the gap between the inner circumferential surface of the outer body 40 and an outer circumferential surface of the inner body 30 is prevented from being exposed. Here, the closure cap 44 may be formed to be separable from the outer body 40.

Since the closure cap 44 is formed to be separable from the outer body 40, when the closure cap 44 is separated from the outer body 40, the inner body 30 is easily inserted into the outer body 40.

Transplantation of a follicle 100 through the manual follicle-transplanting hair transplanter A for increasing a graft survival rate according to the exemplary embodiment of the present invention will be described in detail below.

First, the follicle 100 to be transplanted is contained in the lower end of the needle member 10.

Figure 3:
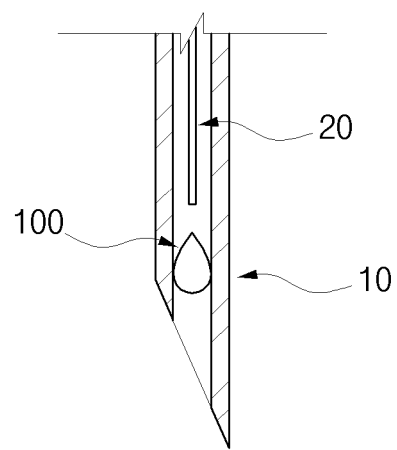
FIG. 3 is an example diagram illustrating containment of a follicle in a needle member according to an exemplary embodiment of the present invention.

In an exemplary embodiment of the present invention, since the inside of the needle member 10 is open, when the follicle 100 is inserted into the lower end of the needle member 10, the follicle 100 may be contained in the lower end of the needle member 10 as shown in FIG. 3.

Next, the lower end of the needle member 10 containing the follicle 100 is inserted into skin of a region of hair loss.

Figure 4:
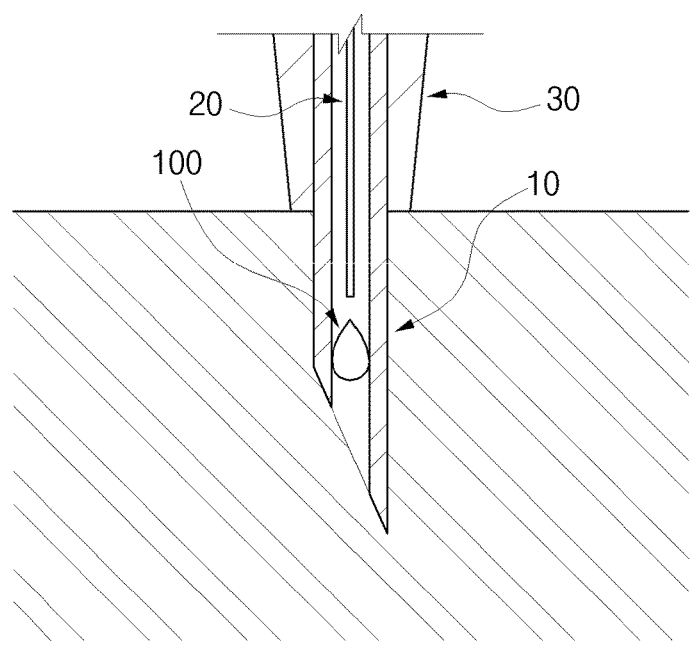
FIG. 4 is an example diagram illustrating insertion of a needle member into skin according to an exemplary embodiment of the present invention.

Since a predetermined length of the lower end of the needle member 10 containing the follicle 100 is exposed from the lower end of the inner body 30 before use, when the lower end of the needle member 10 pierces the skin of the region of hair loss as shown in FIG. 4, the lower end of the needle member 10 is inserted into the skin to a predetermined depth. Accordingly, the follicle 100 contained in the lower end of the needle member 10 is placed in the skin.

Next, the needle member 10 is withdrawn, and the follicle 100 is pressurized by the rod member 20.

Figure 5:
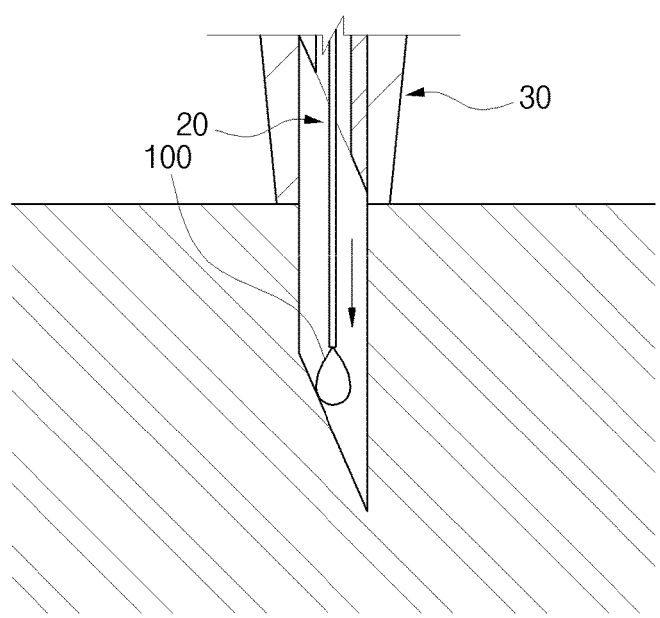
FIG. 5 is an example diagram illustrating pressurization of a follicle through a rod member according to an exemplary embodiment of the present invention.
Figure 6:
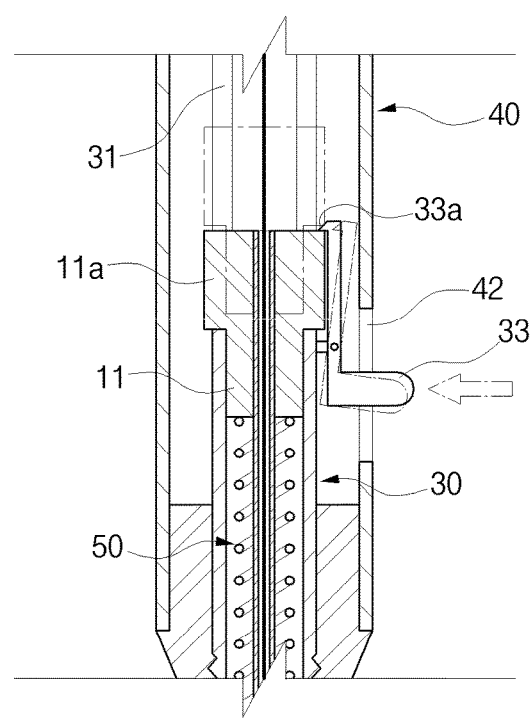
FIG. 6 is an example diagram illustrating a withdrawal of a needle member according to an exemplary embodiment of the present invention.

When the needle member 10 is withdrawn, the lower end of the rod member 20 protrudes from the lower end of the needle member 10 and pressurizes the follicle 100 as shown in FIG. 5. Therefore, while the needle member 10 exits the skin, the follicle 100 is stably embedded in the skin. At this time, the needle member 10 is withdrawn due to pressurization from the outer body 40. In other words, a lower surface of the head 11 of the needle member 10 is in contact with the upper end of the spring 50 supported by the seating surface 32 of the inner body 30, and the upper end of the spring 50 is supported by the support member 33, so that the spring 50 is kept compressed. When the support for the spring 50 through the support member 33 is released by directly pressurizing a part of the support member 33 exposed to the outside of the outer body 40, the compressed spring 50 expands as shown in FIG. 6, and the upper end of the spring 50 pushes up the lower surface of the head 11. Accordingly, the needle member 10 is withdrawn.

The support member 33 is moved outward from the inner body 30 by pressurization from the outer body 40, and the protrusion 33*a* at the upper end of the support member 33 deviates from the upper end of the compressed spring 50. Accordingly, the support for the upper end of the spring 50 is released, and the compressed spring 50 expands and pushes up the lower surface of the head 11. Therefore, the needle member 10 may be withdrawn.

Figure 8:
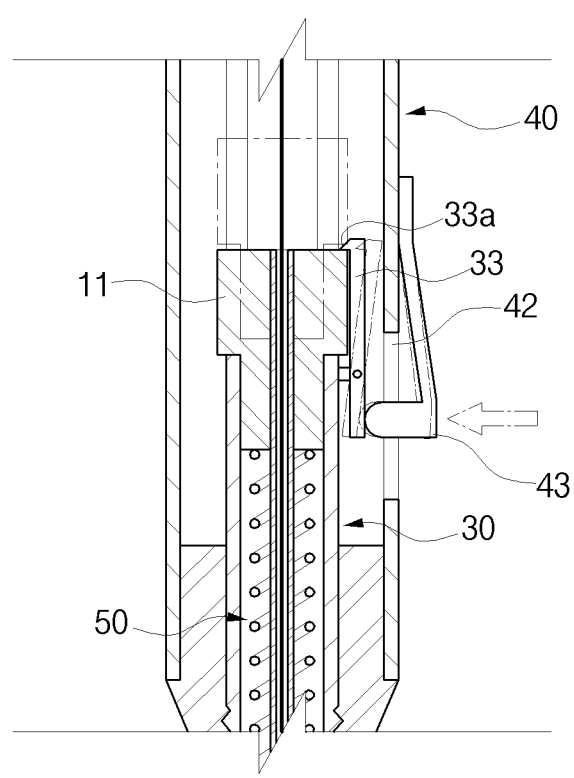
FIG. 8 is an example diagram illustrating indirect pressurization on a support member according to an exemplary embodiment of the present invention.

Also, the lower surface of the head 11 of the needle member 10 is in contact with the spring 50 supported by the seating surface 32 of the inner body 30, and the upper end of the spring 50 is supported by the support member 33, so that the spring 50 is kept compressed. When the support for the spring 50 through the support member 33 is released by indirectly pressurizing the support member 33 through the push member 43 on the outer body 40 as shown in FIG. 8, the compressed spring 50 expands, and the upper end of the spring 50 pushes up the lower surface of the head 11. Accordingly, the needle member 10 is withdrawn.

The support member 33 is moved outward from the inner body 30 by indirect pressurization from the push member 43, and the protrusion 33*a* at the upper end of the support member 33 deviates from the upper end of the compressed spring 50. Accordingly, the support for the upper end of the spring 50 is released, and the compressed spring 50 expands and pushes up the lower surface of the head 11. Therefore, the needle member 10 may be withdrawn.

In this way, the needle member 10 withdraws due to pressurization from the outer body 40. Therefore, during the withdrawal of the needle member 10, unnecessary movement, etc. of the needle member 10 is minimized regardless of a transplantation surgeon's skill or fatigue, and withdrawals of the follicles 100 caused by unnecessary movement, etc. of the needle member 10 are minimized. Consequently, depths of the embedded follicles 100 are uniformized, and also actions of a transplantation surgeon associated with the withdrawal of the needle member 10 are minimized.

As described above, according to the inventive manual follicle-transplanting hair transplanter A for increasing a graft survival rate, the needle member 10 is inserted into skin and then is automatically withdrawn when the compressed spring 50 disposed in the inner body 30 expands, so that the follicle 100 is prevented from withdrawing due to unnecessary movement, etc. of the needle member 10 in the withdrawal process of the needle member 10. Therefore, depths of the follicles 100 transplanted into the skin can be uniformized, and it is possible to maximize a survival rate of the follicles 100. Also, hand movements of a transplantation surgeon are minimized in the withdrawal process of the needle member 10, and it is possible to minimize transplantation surgeon fatigue caused by repeated hand words.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A manual follicle-transplanting hair transplanter for increasing a graft survival rate, the manual follicle-transplanting hair transplanter comprising:

a needle member having a lower end containing a follicle to be transplanted and having a head having a larger diameter than a portion below the head at an upper end thereof;

a rod member inserted into the needle member and having a push portion having a larger diameter than a portion below the push portion at an upper end thereof;

an inner body configured to contain the needle member and limit downward movement of the needle member; and an outer body configured to contain the inner body and limit upward movement of the needle member, wherein the needle member is automatically withdrawn when a spring in a compressed state and disposed in the inner body expands and pushes up a lower surface of the head, wherein the inner body has a support member for supporting an upper end of the spring in the compressed state, wherein the needle member is movable into or out of openings formed in the inner body.

2. The manual follicle-transplanting hair transplanter of claim 1, wherein the head has bumps on two opposite side surfaces.

3. The manual follicle-transplanting hair transplanter of claim 2, wherein the inner body has openings on two opposite side surfaces.

4. The manual follicle-transplanting hair transplanter of claim 1, wherein the inner body has a seating surface for supporting a lower end of the spring in a lower portion thereof.

5. The manual follicle-transplanting hair transplanter of claim 1, wherein the support member is disposed on one side or two opposite sides of the inner body.

6. The manual follicle-transplanting hair transplanter of claim 1, wherein the support member has a protrusion catchable at an upper end of a head portion of the needle member.

7. The manual follicle-transplanting hair transplanter of claim 1, wherein the outer body has a protruding jaw at an inner circumferential surface thereof.

8. The manual follicle-transplanting hair transplanter of claim 1, wherein the outer body has a separable closure cap at a lower end thereof.

* * * * *